United States Patent [19]
Bertola et al.

[11] Patent Number: 5,108,917
[45] Date of Patent: Apr. 28, 1992

[54] PROCESS FOR THE PREPARATION OF IBUPROFEN

[75] Inventors: Mauro A. Bertola, Delft; Marie J. De Smet, Gouda; Arthur F. Marx, Delft, all of Netherlands; Gareth T. Phillips, Kent, United Kingdom

[73] Assignees: Gist-Brocades N.V., Delft; Shell Internationale Research Maatschappij B.V., Den Haag, both of Netherlands

[21] Appl. No.: 212,591

[22] Filed: Jun. 28, 1988

[30] Foreign Application Priority Data

Jul. 1, 1987 [GB] United Kingdom ............... 8715476

[51] Int. Cl.$^5$ ........................... C12P 7/00; C12N 9/00
[52] U.S. Cl. .................................. 435/136; 435/141; 435/196; 435/280; 435/252.1; 435/252.5; 435/823; 435/882
[58] Field of Search ............... 435/136, 141, 196, 280, 435/252.1, 252.5, 823, 882

[56] References Cited

U.S. PATENT DOCUMENTS 4,886,750 12/1989 Bertola et al. ...................... 435/136

FOREIGN PATENT DOCUMENTS 0195717 9/1986 European Pat. Off. .
0196625 10/1986 European Pat. Off. .

OTHER PUBLICATIONS

"Asymmetric Hydrolysis of (±)-alpha-substituted Carboxylic Acid Esters with Microorganism," Agricultural and Biological Chemistry, vol. 45, No. 6, (1981) pp. 1389-1392.

Bergey's Manual of Systematic Bacteriology, vols. 1 & 2, ed. Krieg, pp. 269-271 (vol. 1), pp. 1015-1019 and 1131 (vol. 2).

Primary Examiner—Johnnie R. Brown
Assistant Examiner—Pamela S. Webber
Attorney, Agent, or Firm—Fleit, Jacobson, Cohn, Price, Holman & Stern

[57] ABSTRACT

A process is provided for the preparation of ibuprofen enriched in R isomer, which comprises subjecting an ester of ibuprofen, to the action of a micro-organism or substances derived thereof, that will stereoselectively hydrolyse the ester to form ibuprofen predominantly having R configuration.

17 Claims, No Drawings

PROCESS FOR THE PREPARATION OF IBUPROFEN

The present invention relates to a process for the preparation of ibuprofen or a salt or ester thereof and particularly to the production of compounds having predominantly the R configuration.

It is known that many biologically active compounds exist as a mixture of stereoisomers. Up to now these mixtures are frequently used as such in agricultural and pharmaceutical applications. Usually the desired biological activity resides mainly in one stereoisomer so that in case of a two stereoisomer mixture the potency of the mixture is reduced to as low as half. However a major reason for the continuous use of mixtures of stereoisomers is that the cost of separation of the stereoisomers exceeds the potential advantage of a possible increase in activity. On the other hand it is apparent that modern pharmacologists are becoming increasingly aware of other implications of the administration of mixtures wherein one or more stereoisomers have to be regarded as impurities that may not have the desired therapeutic effect, and may even have other unwanted physiological effects including toxicity.

The stereoselective preparation of the R-enantiomer of ibuprofen by microbial oxidation of 1-isobutyl-4-(1'-methyloctyl) benzene, an aromatic hydrocarbon which has an appropriate non-functional aliphatic side chain, is described by T. Sugai and K. Mori (Agric. Biol. Chem., 48 (1984) 2501).

R-ibuprofen, the therapeutic inactive isomer, is expected to give less gastrointestinal side effects than the racemate. The antiinflammatory effects are retained by the inversion to the therapeutic active S-isomer in the liver (A. J. Hutt and J. Caldwell, J. Pharm. Pharmacol., 35, (1983) 693).

Therefore there is still a requirement for an industrial scale process giving rise to economically attractive yields for the preparation of R-ibuprofen. The object of the invention is to provide such a process.

As a result of extensive research and experimentation we have now developed an improved synthesis for the preparation of ibuprofen, enriched in the R-enantiomer which comprises subjecting an ester of ibuprofen, wherein the ester is preferably an alkyl group optionally substituted or branched, to the action of a micro-organism or substances derived therefrom, having the ability for stereoselective hydrolysis of the ester of ibuprofen for a period of time such that ibuprofen enriched in R-isomer is formed. After separation of the residue ester of ibuprofen and the resulting ibuprofen enriched in R-isomer, from one another, the ibuprofen may be converted into a salt or ester thereof without losing the enrichment in R-isomer.

By "enriched" in R-isomer, we mean containing predominantly R-isomer i.e. more than 50% by weight R-isomer.

Advantageously a linear alkyl ester of ibuprofen is used, preferably the alkyl group contains 1-5 carbon atoms, more preferably the alkyl group is methyl, ethyl or propyl.

According to a preferred embodiment, the process is carried out with a micro-organism or substance derived thereof such that ibuprofen is formed preferably in at least 80%, more preferably at least 90% by weight in the R-configuration.

It is another object of the invention to provide an enzyme which may be advantageously used in the process of the invention.

A further object of the invention is to provide a process for the preparation of ibuprofen enriched in the S-configuration, preferably having at least 80%, more preferably 90%, in the S-configuration which comprises a process for producing predominantly R-ibuprofen according to the invention, after which the residual ester of ibuprofen is separated from the ibuprofen, the residual ester of ibuprofen now enriched in S-isomer is hydrolysed, and if desired, may be converted into a (pharmaceutically acceptable) salt or ester thereof without losing the S-isomer configuration.

By the term "micro-organism having the ability for stereoselective hydrolysis" we mean micro-organisms such as bacteria, yeasts or fungi. Suitable bacteria are for example those of the genus Bacillus, Staphylococcus and Acetobacter.

Use may be made of mutants derived from these microorganisms as well.

Use may also be made of micro-organisms, which have obtained the ability for stereoselective hydrolysis of the ester of ibuprofen into ibuprofen by the introduction of novel genetic material.

This can be accomplished by isolation of the cloned gene encoding a protein responsible for the stereoselective hydrolysis, an esterase enzyme, from any of the screened micro-organisms followed by the transfer to another micro-organism, particularly to *Escherichia coli*. Other micro-organisms which may be transformed are those of the genus Saccharomyces, Staphylococcus, Kluyveromyces, Bacillus, Aspergillus, Escherichia, Pseudomonas and Streptomyces. Cloned genes may be selected for their ability to encode an enzyme capable of hydrolyzing an ester of β-naphthyl-acetate, naproxen ester or preferably ibuprofen ester. Alternatively they may be selected by cross-hybridization with an already selected gene encoding an esterase, or with a synthetic oligonucleotide designed from the $NH_2$-terminal sequence of the esterase.

The micro-organisms may advantageously be immobilized, for example on a polymer gel. This can be done with living, resting and/or killed cells, but alternatively with an esterase enzyme, which may be purified to a certain extent if a higher specific activity is needed.

Therefore by the term "micro-organisms or substances derived thereof" we mean the micro-organisms, killed, alive or resting cells or extracts thereof, optionally concentrated or purified. It is found that cell hydrolysates or enzyme (preparations) derived or isolated from the cells or killed cells can hydrolyze the R-isomer of the ester of ibuprofen under suitable conditions and such enzymes form a further aspect of the invention. For example, intracellular or extracellular enzymes can be obtained from such microorganisms. The microorganisms or substances derived thereof may be used several times and may be active for at least two weeks.

The hydrolysis of ester into the R-isomer of ibuprofen takes place in suitable buffers as well as in physiological salts. After storage the induced cells are found to be directly capable of hydrolysing the ester into the R-isomer of ibuprofen.

Cultures of species Bacillus which may be used in the invention include cultures of *Bacillus cereus*, preferably species *Bacillus cereus* (a sample of this species is deposited with the ATCC under the accession number 9139), *Bacillus cereus* Nap 1-1 (a sample of this species is deposited with the CBS under the accession number 338.87). *Bacillus cereus* Nap 2-1 (a sample of this species is deposited with the CBS under the accession number 339.87) and *Bacillus species* Nap 4M (a sample of this species is deposited with the CBS under the accession number 342.87). Cultures of species Staphylococcus which may be used in the invention include cultures of species *Staphylococcus aureus* Nap 2-5 (a sample of this species is deposited with the CBS under the accession number 340.87) and *Staphylococcus aureus* Nap 3-8 (a sample of this species is deposited with the CBS under the accession number 341.87). Cultures of species Acetobacter which may be used in the invention include cultures of species *Acetobacter xylinum L*. Parish (a sample of this species is deposited with the CBS under the accession number 343.87).

According to a preferred embodiment of the present invention, a micro-organism having the ability to hydrolyse the ester of ibuprofen into ibuprofen having at least 80% by weight R-configuration, may be cultured for about 0.5 to 10 days. The cells may be then suspended in a liquid nutrient medium and the ester of ibuprofen is subjected to the action of the cells. Alternatively the cells may be killed for example suspended in a lysis medium, and the ester of ibuprofen is then subjected to the action of the substances released from the lysed cells.

After the abovementioned cultivation for about 0.5 to 10 days, the cells may be isolated from the culturing medium before they are suspended in the liquid nutrient medium or in a lysis medium.

To grow the micro-organisms used for the selective hydrolysis of the ester of ibuprofen, ordinary culture media containing an assimilable carbon source (for example glucose, lactate, sucrose, etc.), a nitrogen source (for example ammonium sulphate, ammonium nitrate, ammonium chloride, etc.), with an agent providing an organic nutrient source (for example yeast extract, malt extract, peptone, meat extract, etc.) and an inorganic nutrient source (for example phosphate, magnesium, potassium, zinc, iron and other metals in trace amounts) may be used.

A Jap medium optionally enriched with one or more ingredients may be used as a suitable culture medium. A Jap medium of the following composition may be used: soybean flour (30 g/l), sodium nitrate (7.5 g/l), ferrous sulphate.7H$_2$O (0.28 g/l), sodium citrate (6 g/l) and fructose (12.5 g/l), the pH adjusted to 7.2. Before use the medium should be sterilized e.g. for 20 minutes at 120° C.

Another preferred culture medium is a TSB-medium 2×, optionally enriched with one or more ingredients. A medium consisting of 60 g/l trypticase soy broth (Oxoid ®) may be used. Before use the medium should be sterilized e.g. for 20 minutes at 120° C. Another preferred medium is 2×TY optionally enriched with one or more ingredients. A medium consisting of Tryptone (Difco ®) 30 g/l, Yeast extract (Difco ®) 20 g/l, NaCl 3 g/l, (NH$_4$)$_2$HPO$_4$ 1 g/l and (NH$_4$)$_2$SO$_4$ 1 g/l at pH 6.8 can be used. Before use the medium should be sterilized e.g. for 30 minutes at 110° C. A more preferred culture medium is a skimmed milk medium optionally enriched with one or more ingredients. A skimmed milk medium of the following composition may be used: 10% skimmed milk from skimmed milk-powder, which should be sterilized e.g. for 30 minutes at 110° C. before use.

Enrichments to the skimmed milk medium can be, for example 0.5% lactate or PSIII salts or combinations thereof. PSIII salt medium of the following composition may be used: potassium dihydrogen phosphate (2.1 g/l), ammonium monohydrogen phosphate (1.0 g/l), ammonium sulphate (0.9 g/l), potassium chloride (0.2 g/l), sodium citrate (0.29 g/l), calcium sulphate.2H$_2$O (0.005 g/l), magnesium sulphate.7H$_2$O (0.2 g/l), ammonium ferrous sulphate.6H$_2$O (2.5 mg/l), zinc sulphate.7-H$_2$O (0.5 mg/l), manganese chloride.4H$_2$O (0.3 mg/l), copper sulphate.5H$_2$O (0.15 mg/l), cobalt chloride.6-H$_2$O (0.15 mg/l), ortho-boric acid (0.05 mg/l), sodium molybdate.2H$_2$O (0.055 mg/l) and potassium iodide (0.1 mg/l), the pH adjusted to 6.8. Before use the PSIII salt medium should be sterilized e.g. for 20 minutes at 120° C.

A temperature of 0° to 45° C. and a pH of 3.5 to 9 is preferably maintained during the growth of the micro-organisms. More preferably the micro-organisms are grown at a temperature of 20° to 37° C. and at a pH of 5 to 9.

The aerobic conditions required during the growth of the micro-organisms can be provided according to any of the well-established procedures, provided that the supply of oxygen is sufficient to meet the metabolic requirement of the micro-organisms. This is most conveniently achieved by supplying oxygen, suitably in the form of air and optionally at the same time shaking or stirring the reaction liquid. During the hydrolysis of the ester of ibuprofen into ibuprofen the micro-organisms can be in a growing stage using an above-mentioned ordinary culture medium or can be preserved in any system (medium or buffer) preventing degradation of enzymes.

During the hydrolysis of the ester of ibuprofen into ibuprofen, an ordinary culture medium may be used containing an assimilable carbon source when required (for example glucose, lactate, sucrose, etc.), a nitrogen source when required (for example ammonium sulphate, ammonium nitrate, ammonium chloride, etc.), with an agent providing an organic nutrient source when required (for example yeast extract, malt extract, peptone, meat extract, etc.) and an inorganic nutrient source when required (for example phosphate, magnesium, potassium, zinc, iron and other metals in trace amounts).

Preferably, during the hydrolysis of the ester of ibuprofen into ibuprofen, a Jap medium (as described above) optionally enriched with one or more ingredients may be used. More preferably a skimmed milk medium (as described above) optionally enriched with one or more ingredients may be used.

The micro-organisms can be kept in the non-growing stage for example by exclusion of the assimilable carbon source or by exclusion of the nitrogen source. A temperature of 0° to 45° C. and a pH of 3.5 to 9 is preferably maintained during this hydrolysis stage.

During the hydrolysis stage the micro-organisms are preferably kept at a temperature of 20° to 37° C. and a pH of 5 to 8. The aerobic conditions required during this stage can be provided according to any of the well-established procedures, provided that the supply of oxygen is sufficient to meet the metabolic requirement of the micro-organisms. This is most conveniently achieved by supplying oxygen, suitably in the form of air and optionally, at the same time, shaking or stirring the reaction liquid. During the conversion of the ester of ibuprofen into ibuprofen by resting cells, cell hydrolysates or enzyme preparations derived from the cells an ordinary buffered aqueous solution may be used. A temperature of 0° to 45° C. and a pH of 3.5 to 7.0 is maintained during the enzymatic conversion. Preferably the aqueous solution is kept at a temperature of 20°–40° C. and a pH of 7.0 to 9.5. More preferably the pH is maintained at 7.0 to 9.5 by the addition of a base such as NaOH or $NH_4OH$. The ibuprofen produced by the micro-organisms or substances derived thereof, as mentioned above, can be recovered and purified according to any of the procedures known per se for such products.

The micro-organisms can be kept on agar slants, frozen in 50% glycerol or lyophilised. If required, precultures of these micro-organisms can be made according to any of the well-established procedures, for example the micro-organisms can be incubated in bouillon or in BHI for 24 hours at 30° C. in a rotary shaker. A bouillon medium of the following composition can be used: Lab Lemco L 29 (meat extract, Oxoid ®) (9 g/l), Bactopepton (10 g/l) and sodium chloride (5 g/l), the pH adjusted to 7.6. Before use this medium should be sterilized e.g. for 20 minutes at 120° C.

A BHI (brain-heart infusion) medium containing 0.037 g/l BHI (Oxoid ®), the pH adjusted to 7.0, can be used. Before use this medium should be sterilized e.g. for 20 minutes at 120° C.

A YEPD medium can be used of the following composition: 20 g/l bactopeptone, 10 g/l yeast extract, 20 g/l glucose. Before use this medium should be sterilized e.g. for 30 minutes at 110° C.

A further aspect of the present invention provides pharmaceutical compositions comprising ibuprofen obtained according to the present invention together with a pharmaceutically acceptable carrier.

The present invention will be further described with reference to the following Examples, without restricting the scope of the present invention to these Examples.

EXAMPLE 1

The micro-organisms mentioned in Table 1 below were grown in 25 ml of BHI-medium and kept in 100 ml flasks on a rotary shaker at 30° C. for 24 hours. After full growth, the cultures were diluted ten times in 25 ml of 10% skimmed milk medium and 20 µl R/S methyl ester of ibuprofen (methyl-2-(4-isobutyl-1-phenyl)propionate) were added. The cultures were then reincubated for 24 hours.

After this incubation period, the cultures were acidified with $H_3PO_4$ to pH 2.0 and extracted with dichloromethane. The ibuprofen present in the extracts was then converted into a naphthalene-methylamide derivative in order to determine its enantiomeric purity.

To 3 ml extract 200 µl of a solution of 2-bromo-1-methylpyridine iodide dissolved in dimethylformamide (50 mg/ml) and 200 µl of a solution of 1-naphthalenemethylamine dissolved in $CH_2Cl_2$ (100 mg/ml) were added and allowed to react for 5 minutes at 22° C. The reaction mixture was dried under $N_2$ at 60° C. The remaining residue was dissolved in 3 ml of isooctane/$CH_2Cl_2$ (2:1 v/v) and extracted after the addition of 2 ml of 1N $H_2SO_4$.

The organic layer was analysed on HPLC using a chiral DNBPG (dinitrobenzoyl phenylglycine) column eluted with isooctane/isopropyl-alcohol/methanol (97/2/1 v/v).

The results are presented in Table 1.

TABLE 1

Enantiospecific hydrolysis of ibuprofen methyl ester.

| Micro-organism | Ibuprofen formed mg/culture** | % S | % R |
|---|---|---|---|
| Acetobacter xylinum L. Parish (CBS 343.87) | 4.0–5.0 | 16* | 84* |
| Bacillus cereus (ATCC 9139) | 2.0–2.5 | 19 ± 2 | 81 ± 2 |
| Bacillus cereus Nap 1-1 (CBS 338.87) | 0.8–3.5 | 10 ± 2 | 90 ± 2 |
| Staphylococcus aureus Nap 2-5 (CBS 340.87) | 3.0–3.5 | 7 ± 3 | 93 ± 3 |
| Staphylococcus aureus Nap 3-8 (CBS 341.87) | 3.2–4.5 | 5 ± 3 | 95 ± 5 |
| Bacillus spec. Nap 4M (CBS 342.87) | 1.8–2.0 | 27 ± 2 | 73 ± 2 |

The standard deviations have been derived from 3–6 values.
*Value obtained from a duplicate experiment.
**Since, in certain cases, the variability in quantities ester hydrolysed was relatively large, no mean values are given. The values presented here are the minimal and maximal value found in different experiments.

EXAMPLE 2

The organisms mentioned in Table 2 were grown as described in Example 1. Instead of the methyl ester of ibuprofen, as described in Example 1, 20 µl of the R/S ethyl ester were added.

After the incubation period of 24 hours, the cultures were acidified, extracted and the ibuprofen formed derivatised as described in Example 1.

The results are presented in Table 2 below.

TABLE 2

Enantiospecific hydrolysis of ibuprofen ethyl ester.

| Micro-organism | Ibuprofen formed mg/culture*** | % S | % R |
|---|---|---|---|
| Acetobacter xylinum L. Parish (CBS 343.87) | 2.0–4.0 | 8 ± 2 | 92 ± 2 |
| Bacillus cereus (ATCC 9139) | 3.5–3.9 | 5 ± 1 | 95 ± 1 |
| Bacillus cereus Nap 1-1 (CBS 338.87) | 0.8–5.0 | 6 ± 1 | 94 ± 1 |
| Bacillus cereus Nap 2-1 (CBS 339.87) | 0.3–5.3 | 7 ± 3 | 93 ± 3 |
| Staphylococcus aureus Nap 2-5 (CBS 340.87) | 0.13–0.25 | 0* | 100* |
| Staphylococcus aureus Nap 3-8 (CBS 341.87) | 0.13–0.25 | 0* | 100* |
| Bacillus spec. Nap 4M (CBS 342.87) | 4.4–4.6 | 9** | 91** |

The standard deviations have been derived from 3–6 values.
*This value represents the mean of a duplicate result.
**Value obtained from a single experiment.
***Since, in certain cases, the variability in quantities ester hydrolysed was relatively large, no mean values are given. The values presented here are the minimal and maximal value found in different experiments.

EXAMPLE 3

Molecular cloning of the gene responsible for the enantiospecific hydrolysis of R-ibuprofenmethyl ester A plasmid, pIBU1, containing a chromosomal DNA fragment of Staphylococcus aureus Nap 2-5 (CBS 340.87) can be constucted as described below. For employment of general cloning techniques, the handbook of T. Manatis et al., 1982, Molecular Cloning, Cold Spring, Harbour Laboratory, can be used as a reference. DNA modifying enzymes can be obtained from commercial suppliers and used according to the manufacturers' instructions. Partially Sau3A digested Staphylococcus aureus Nap 2-5 total DNA (e.g. size fraction from 1 to 5 kb) can be ligated into an appropriate cloning vector, for instance pUN121 digested with Bcl1 (Nilsson et al., 1983, Nucleic Acids Res. 11, p. 8019). The DNA mixture can be transformed into *Escherichia coli* DH1 (ATCC 33849) in order to generate a gene library of *Staphylococcus aureus* Nap 2-5. Transformants with an ampicillin and tetracycline resistent phenotype can be stored and replica-plated according to J. P. Gergen et al. (Nucleic Acids Res. 7, p. 2115, 1979). Replicated colonies can be screened with a soft agar overlay of essentially the following composition: 0.5% lowmelting agarose, 0.5M potassium phosphate (pH 7.5), 0.5 mg/l β-naphthyl acetate (obtained from Sigma) and 0.5 mg/ml fast-blue (obtained from Sigma). Within a few minutes colonies with esterase or lipase activity will colour purple. Selected colonies can be grown overnight in 2×YT medium (16 g/l bactotryptone, 10 g/l yeast extract, 5 g/l NaCl) and subsequently assayed for their ability to convert R-ibuprofen methyl ester according to the method of Example 1 (with BHI-medium substituted by 2×YT medium). With the aid of this test colonies harbouring recombinant plasmids carrying the gene encoding the esterase specific for R-ibuprofen can be isolated.

Alternatively, if no positive clones are detected, the gene library can be screened by hybridisation with oligonucleotides designed from the $NH_2$-terminal amino-acid sequence of the esterase or by immunological screening with antibodies directed against the esterase. The R-ibuprofen esterase encoding plasmid is called pIBU-1. Subsequently the esterase gene can be recloned into an appropriate host in order to enhance the expression level of the esterase. This can be achieved by digestion of pIBU-1 partially with Sau3A followed by ligation of an esterase containing Sau3A fragment into the BAM M1 site of pUB110. Recombinant plasmids can be transformed into *Bacillus subtilis* 1A-40 (Bacillus Stock Center B.G.S.C. 1A40) (S. Chang and S. N. Cohen, Mol. Gen. Genet. 168, p. 111, 1979) or *Bacillus subtilis* 1S-53 (Bacillus Stock Center B.G.S.C. 1S-53) (Rec. DNA Bull. 4, p. 1, 1981). Neomycin resistant transformant can be tested for their ability to hydrolyze R-ibuprofen methyl ester according to the method of Example 1. Since it is known that genes originating from the gram-positive bacteria *Staphylococcus aureus* are well expressed in the gram-positive *Bacillus subtilis* (Gene 48, p. 93, 1986) it can be expected that the multicopy character of the plasmid which encodes the esterase will lead to a high production of the esterase in *Bacillus subtilis* 1A-40 and *Bacillus subtilis* 1S-53. Ultimately the productivity can be improved by fusion of the esterase gene to a strong *Bacillus* promoter.

We claim:

1. A process for the production of ibuprofen containing more than 50% by weight R isomer which consists of subjecting an ester of ibuprofen to the action of a micro-organism or enzyme preparation derived therefrom that will stereoselectively hydrolyse the ester to form ibuprofen having more than 50% by weight R configuration.

2. A process according to claim 1 wherein the ibuprofen having more than 50% by weight R configuration is separated from residual ester having more than 50% by weight S configuration.

3. A process according to claim 2 wherein the separated ibuprofen of more than 50% by weight R configuration is converted into a salt or ester of ibuprofen having more than 50% by weight R configuration.

4. A process according to claim 2 wherein the residual ester having more than 50% by weight S configuration is hydrolysed to form ibuprofen.

5. A process according to claim 1 wherein the ester of ibuprofen is an alkyl ester.

6. Process according to claim 5, wherein the alkyl group is optionally substituted or branched.

7. Process according to claim 5, wherein the ester is a methyl or an ethyl ester.

8. Process according to claim 1 wherein at least 80% by weight of ibuprofen is formed in the R-configuration.

9. Process according to claim 1 wherein the micro-organism is used in immobilized form either as a living cell, as a killed cell or as a resting cell.

10. A process according to claim 1 wherein a substance is released from the microorganism and is used to stereoselectively convert the ibuprofen ester into the ibuprofen having more than 50% by weight R configuration.

11. A process according to claim 1, wherein said micro-organism is a member selected from the group consisting of bacteria, yeasts and fungi.

12. Process according to claim 1 wherein said micro-organism is a micro-organism transformed with a DNA fragment encoding esterase having the ability for stereoselective hydrolysis of R/S ibuprofen ester.

13. A process according to claim 4 further comprising the step of converting the ibuprofen obtained by hydrolysing the residual ester into a salt or ester thereof.

14. A process according to claim 11, wherein said micro-organism is a bacterium belonging to a genus selected from the group consisting of Bacillus, Staphylococcus and Acetobacter.

15. A process according to claim 14, wherein said micro-organism is selected from the group consisting of *Bacillus cereus* and *Staphylococcus aureus*.

16. A process according to claim 14, wherein said micro-organism is selected from the group consisting of *Bacillus cereus* (ATCC 9139), *Bacillus cereus* Nap 1-1 (CBS 338.87), *Bacillus cereus* Nap 2-1 (CBS 339.87), *Bacillus species* 4M (CBS 342.87), *Staphylococcus aureus* Nap 2-5 (CBS 340.87), *Staphylococcus aureus* Nap 3-8 (CBS 341.87) and *Acetobacter xylinum* L. Parish (CBS 343.87).

17. A process according to claim 12, wherein the DNA fragment is derived from a member selected from the group consisting of Bacillus, Staphylococcus and Acetobacter species.

* * * * *